(12) United States Patent  (10) Patent No.: US 7,130,050 B2
Sacchi                    (45) Date of Patent:    Oct. 31, 2006

(54) DEVICE OF VERIFYING AND READING COLOR, AND A PROCESS OF VERIFYING AND READING COLOR IN LIQUIDS

(76) Inventor: Fabricio de Araújo Sacchi, Rua Dr. Cintra Gordinho, 156, Alto da Lapa, 0508-001, São Paulo (B ( * ) Notice: Subject to any disclaimer, the term of this patent is extended or adjusted under 35 U.S.C. 154(b) by 247 days.

(21) Appl. No.: 10/923,104

(22) Filed: Aug. 19, 2004

(65) Prior Publication Data

US 2006/0039000 A1    Feb. 23, 2006

(51) Int. Cl.
G01J 3/50 (2006.01)
G01N 21/25 (2006.01)

(52) U.S. Cl. .................. 356/409; 356/406; 250/226

(58) Field of Classification Search ............... 356/406, 356/407, 409–411
See application file for complete search history.

(56) References Cited

FOREIGN PATENT DOCUMENTS

JP           64-31037    * 2/1989  .................. 356/406

* cited by examiner

Primary Examiner—F. L. Evans
(74) Attorney, Agent, or Firm—TraskBritt, P.C.

(57) ABSTRACT

A device for verifying and reading color, particularly used in reading the color of a liquid, the device comprising: a) a guide tube (10); and (b) at least one pair of liquid detection sensors (20), associated to the guide tube (10), the device comprising pairs of spectral-frequency emitting sensors (30, 31, 32) and spectral-frequency receiving sensors (30', 31', 32'), associated to the guide tube (10) and oppositely aligned, the spectral-frequency emitting sensors (30, 31, 32) being activated by detection of the liquid by the detection sensors (20). A process of verifying and reading color in liquids by means of a device of verifying and reading color, the process comprising the following steps: (i) calibrating the pairs of spectral-frequency emitting sensors (30, 31, 32) and the spectral-frequency receiving sensors (30', 31', 32'); (ii) detecting the liquid by means of the detection sensor (20); (iii) emitting photons at determined frequency ranges of the spectrum by means of the spectral-frequency emitting sensors (30, 31, 32); (iv) receiving the photons by means of the spectral-frequency receiving sensors (30', 31', 32'); and (v) reading the frequency received and comparing it with pre-established frequencies.

20 Claims, 2 Drawing Sheets

DEVICE OF VERIFYING AND READING COLOR, AND A PROCESS OF VERIFYING AND READING COLOR IN LIQUIDS

BACKGROUND

1. Field of the Invention

The present invention relates to a device of verifying and reading color, usable in conjunction with methods of measuring liquids, especially combustible liquids, in order to verify possible alterations through the change in color, and a method of verifying and reading color in liquids.

2. State of the Art

The large amount of fuel that is daily adulterated is widely known and reaches about 13% on average, varying from 18% to 9% depending upon the region, for sales volumes about 93 million cubic meters in 1999 and 90 million cubic meters in 2000 in Brazil.

This problem is also found in various parts of the world as a function of the high aggregated value of combustible products, which makes them extremely attractive for commerce and also for alterations that impair the quality of the products. In this regard, there is a great difficulty at present in immediately proving adulterations, due to the delay in analysis and the large sales turnover of a reselling station.

According to data obtained at the ANP (National Petroleum Agency), there are on the Brazilian market: 243 Petroleum Distributors, 38,000 filling stations and 100,000 tanks. These data show the impossibility of controlling, through chemical analyses or the like, the quality of fuels from the moment of refining and distributing them until the act of buying the product by the consumer. However, this incapability of controlling the quality and pureness of fuels results in a stimulus for adulteration and the consequent illicit increase in sales.

There is a need for control also in the situations of constant recharges of liquid products. In this case, besides measuring the cubic volume contained in the tanks, it becomes necessary to verify the maintenance of the standard of the liquid to be supplied.

There are many ways of identifying the quality and pureness of the fuel, as for example, the physical-chemical analysis that makes a survey of the various components existing in the products and thus establishes criteria for accepting or rejecting the product in the tank. This process is usually employed in fuel distributing companies, so as to evaluate the maintenance of the standards of quality of their products at the reselling stations, and consists in collecting samples of fuel and mixture of this sample with reactants, so as to establish its composition.

However, in order to prevent frauds, that is, mixture of a fuel with other products after the physical-chemical analysis has been carried out, this analysis should be made in a continuous and uninterrupted way, also at the reselling stations, which is excessively expensive and unfeasible.

In many situations, a fuel reselling station commercializes a large amount of products daily, somewhat above 24 cubic meters (24,000 liters) of a determined type of fuel, for example, gasoline. For various reasons, the reseller intends to purchase 10 cubic meters (10,000 liters) of fuel from another distributing company, which is not the same as that of the reselling company. This product from a third party often does not have any invoice and, since this is not a reliable distributing company, this is often a product of very poor quality, having physico-chemical characteristics quite different from those of the products which this reselling station already has in its tank, and the tank containing the product of good quality already existing therein will receive that of unreliable quality, thus mixing the two products.

The volant unit of the company in charge of the inspection of products of the product-analysis program goes to the selling station at a determined time of day and makes the tests and the physico-chemical analysis, finding and attesting that the products stocked at that establishment are in accordance with the standards of quality determined by the company. At the time of inspection, the storing tank contains only 1 cubit meter (1,000 liters) of fuel from the company itself, which, due to the large volume of sales, will be sold out in a few hours. Once the inspection has been completed, the inspector of the company goes to another station to inspect the product, in order to fulfill his daily visits.

After the inspection and after the fuel of this tank has been sold out, the reselling station receives 10 cubit meters (10,000 liters) of the product from a different origin, which is added to the tank of the example, which is totally empty already, containing only its ballast of 250 liters. The reselling station continues with the regular sales of the adulterated product and, due to its large capacity of sales, in only 10 hours the tank is again empty and needs to be refilled. This time, however, the product is requested to the distributing company.

Thus, when inspection made on the next day the tank is already filled with the product from the distributing company itself and, therefore, the analyses will again indicate that the products sold by the reselling station of the example are totally regular. However, the reselling station would have sold 10,000 liters of adulterated fuel to a large number of consumers, who, without any possibility of reaction or protection, were cheated upon buying products with quality different from that for which they had looked and paid.

Besides the consumer, the distributing company too is seriously prejudiced, since, besides failing to gain regular profits by selling its products, it has expenses with the quality inspection program, which may be questioned, and this would impair its institutional image of a reliable and competent company.

Another important characteristic existing in the products at present is the controlled mixture of colored additives, in order to differentiate products, for instance, in the case of additive-containing gasoline and high octane solid gasoline. This coloring by means of additives also enables visual identification on the part of the consumer who is buying the product.

In this regard, we can observe that there is gasoline of red coloring, which is distinguished form alcohols having greenish color, and so on with other fuels.

Each fuel supplier tries to assign to it mark an exclusive coloring, so as to differentiate it from that of the competitors. This fact also may be proven by installing transparent tubes close to the filling nozzle of the filling station, thus enabling immediate identification by the consumer.

Obviously, there are details in which the consumer's perception cannot detect, such as suave graduations of color or even clarification of adulterated products, since it is not possible, at present, to provide the consumer with standardization, because the slight differences in the coloring of the fuel are imperceptible to the human eye.

SUMMARY OF THE INVENTION

An objective of the present invention is to provide a system of verifying and reading the coloring of fuels on the basis of specific algorithms, the purpose of which is to detect irregularities that may result from adulterations.

Another objective of this invention is to provide a method of verifying and reading the color in liquids by means of the device of verifying and reading color.

The present invention has the objective of providing a device of verifying and reading color, particularly used in reading the color of a liquid, this device being provided with:

(a) a guide tube; and
(b) at least one pair of liquid detection sensors, associated to the guide tube, the device comprising pairs of spectral-frequency emitting sensors and spectral-frequency receiving sensors, associated to the guide tube and aligned in an opposite way, the spectral-frequency receiving sensors being activated by detection of the liquid by the detection sensors.

It is also an objective of this invention to provide a method of verifying and reading color in liquids, comprising the following steps:

(i) calibrating the pairs of spectral-frequency emitting sensors and the spectral-frequency receiving sensors;
(ii) detecting the liquid by means of a detection sensor;
(iii) emitting photons at determined frequency ranges of the spectrum by means of the spectral-frequency emitting sensors;
(iv) receiving the photons by means of the spectral-frequency receiving sensors; and
(v) reading the frequency received and comparing it with pre-established frequency ranges.

BRIEF DESCRIPTION OF THE DRAWINGS

The present invention will now be described in greater detail with reference to an embodiment represented in the drawings. The figures show.

DETAILED DESCRIPTION OF THE INVENTION

Figure 1:
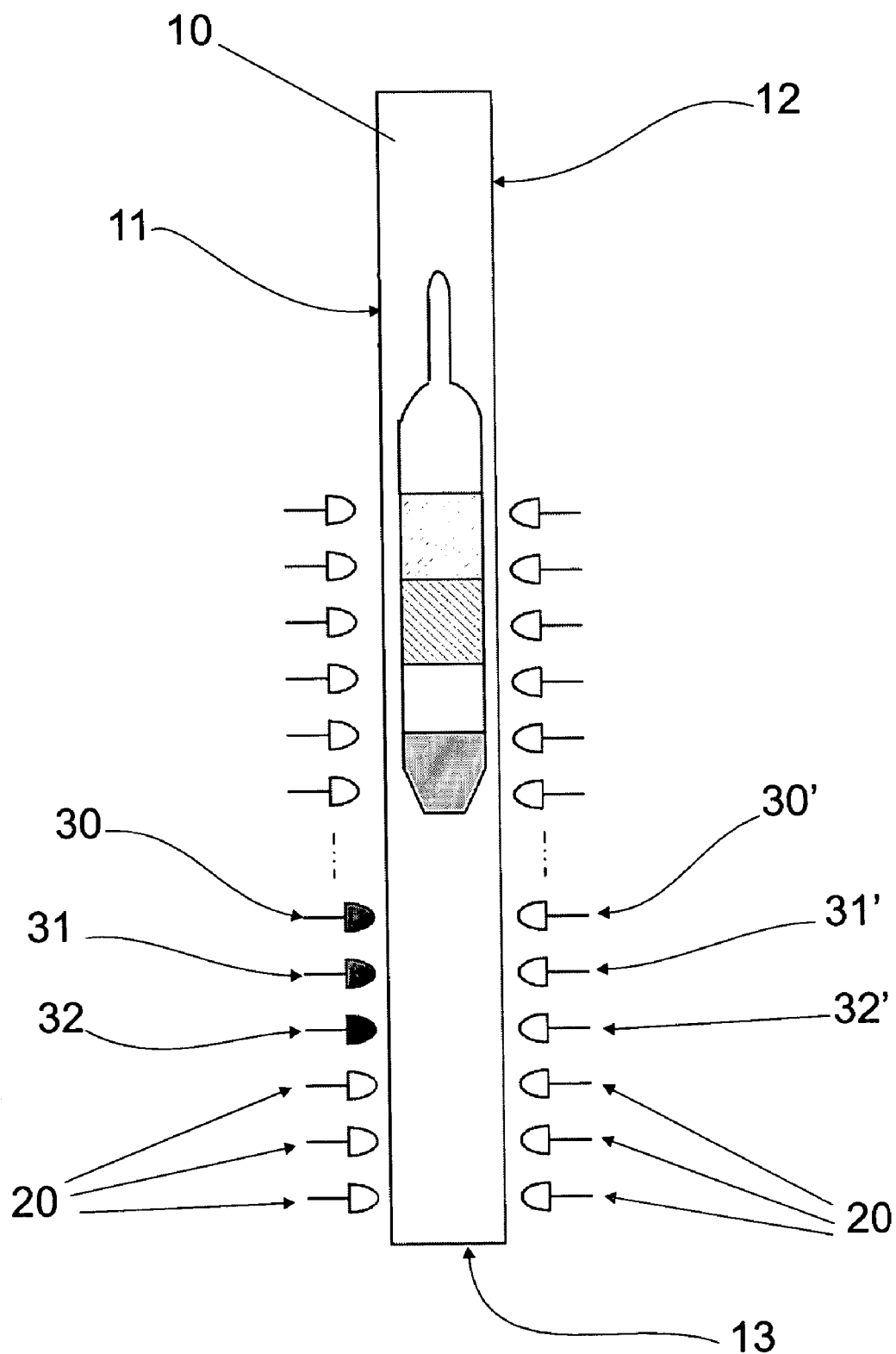
FIG. 1 is a schematic view of the device of the present invention.

As can be seen in FIG. 1, the device for verifying and reading color in liquids is provided with a guide tube 10, formed by a first surface 11 and a second surface 12, substantially parallel to each other, and a lower boundary 13.

At least one pair of liquid detection sensors 20 is associated to the guide tube 10, one of the sensors being arranged on the first surface 11 and the other on the second surface 12, so as to remain at the same height of the sensor arranged on the first surface 11. Preferably, three pairs of detection sensors 20 are provided close to the lower boundary 13 of the guide tube 10.

Further, the device for verifying and reading color comprises pairs of spectral-frequency emitting sensors 30, 31, 32, and spectral-frequency receiving sensors 30', 31', 32', also associated to the guide tube 10, the spectral-frequency emitting sensors 30, 31, 32 being associated, equidistant from each other, to the first surface 11 of the guide tube 10, and the spectral-frequency receiving sensors 30', 31', 32' are also associated, equidistant from each other, to the second surface 12 of the guide tube 10.

The pairs of spectral-frequency emitting sensors 30, 31, 32 and spectral-frequency receiving sensors 30', 31', 32' are oppositely aligned and arranged adjacent to the detection sensors 20, so as to remain most of the time submerged in the liquid to be verified.

The three spectral-frequency emitting sensors 30, 31, 32 are light-emitting sensors (LEDS) different from each other, each spectral-frequency emitting sensors 30, 31, 32 emitting photons at a determined frequency range of the spectrum of luminous frequency.

Taking for base that the colors of the spectrum can be decomposed in three basic colors, red, green and blue, there are disposed a first spectral-frequency emitting sensor 30 which emits photons at the red-color frequency range, a second spectral-frequency emitting sensor 31 which emits photons at the blue-color frequency range, and a third spectral-frequency emitting sensor 32 which emits photons at the green-color frequency range. In this way, each frequency range emitted by a spectral-frequency emitting sensor 30, 31, 32 corresponds to a color.

The guide tube 10 is submerged into a liquid provided with coloring, preferably a combustible-type liquid, so that its lower boundary 13 remains parallel to the bottom of the container or tank that contains this liquid.

The detection sensors 20 emit and receive signals constantly, in order to detect the presence of water in the tank that holds the combustible liquid. The presence of water is detected by positioning, between the pairs of detection sensors 20, a totally opaque buoy (not shown) with a height greater than the distance between two receiving and consecutive detection sensors 20, in order to occur a complete interruption of the beam emitted by the emitting and also consecutive detection sensors 20. The function of this opaque buoy is only to float over the water that may be present in the tank and interrupt one, two or more beams emitted by the detection sensors 20, in order to recognize the presence of water. In this sense, in order to ensure that this buoy remains floating over the water, it is sized in such a way that its specific density will be lower than the specific density of the water, however, higher than the specific density of the combustible liquid, thus guaranteeing the positioning of this buoy close to the bottom of the tank.

In turn, the spectral-frequency emitting sensors 30, 31, 32 are also continuously actuated, emitting the respective spectral frequencies through the liquid, so as to detect possible variations of color.

The spectral-frequency receiving sensors 30', 31', 32' are also different from each other, in order for each spectral-frequency receiving sensor 30', 31', 32' to receive photons emitted by its correspondent spectral-frequency emitting sensors 30, 31, 32.

Thus, the liquid into which the guide tube 10 is submerged actuates as a filter for each of the three basic colors chosen. If this liquid is predominantly red, there will be a small attenuation of the red-color emitter and a greater attenuation in the other colors. Therefore, the intensity in reception of the photons frequency ranges by the spectral-frequency receiving sensors 30', 31', 32' is variable as a function of the coloring of the liquid to be verified.

When the device for verifying and reading color is submerged into the liquid to be verified and read, the process of verifying and reading color in liquids begins, which comprises the following steps:

(i) calibrating the pairs of spectral-frequency emitting sensors 30, 31, 32 and the spectral-frequency receiving sensors 30', 31', 32';
(ii) detecting the liquid by means of a detection sensor 20;

(iii) emitting photons at determined frequency range of the spectrum by means of the spectral-frequency emitting sensors 30, 31, 32;

(iv) receiving the photons by means of the spectral-frequency receiving sensors 30', 31', 32'; and (v) reading the frequency received and comparing it with preestablished frequency ranges.

In order to initiate the process, a calibration is made.

Calibration Logic

The calibration consists in adjusting the gain of the spectral-frequency emitting sensors 30, 31, 32 and in adjusting the gain of the spectral-frequency receiving sensors 30', 31', 32' by means of amplifying electronic circuits and so as to obtain the best light transfer without saturation.

For this purpose, the system will execute the calibration obeying the following steps for each of the three emitting sensors or color LEDs:

Step 1

Starting from unitary gains in both the emitting sensor 30, 31, 32 and the receiving sensor 30', 31', 32', the reading of the emitting sensor 30, 31, 32 begins. The gain of the emitting sensor 30, 31, 32 is successively increased so as to reach the maximum reading. When the gain of the emitting sensor 30, 31, 32 reaches its maximum point, the successive increase in gain of the receiving sensor 30', 31', 32' begins, also so as to reach the maximum reading, that is, maximum light intensity. In this way, one obtains the Maximum Value.

Step 2

The emitting sensor 30, 31, 32 is totally turned off (total absence of light) and the reading of the maximum value obtained at the receiving sensor 30', 31', 32' is carried out, whereby one obtains the minimum reading, or a Minimum Value.

With these values obtained, one can determine the transfer curve of the emitter-receiver pair, thereby guaranteeing the calibration of each pair.

It should be pointed out that this measurement should be carried out in a totally transparent aqueous medium, so as to maintain the refraction index of the medium.

Once the device for verifying and reading color has been calibrated, the step of determining the verification and reading parameters begins, from the reading of standard color of liquids and from the emission of standard values.

In case there is liquid inside the container and once the device has requested the adoption of this measurement obtained as being standard, the latter will verify the composition of the liquid product, obtaining as a result three measurements of luminous intensity, one for each color, respectively. These measurements are considered standard values.

Once the standard values have been obtained, it is possible to evaluate the possible deviations in the process of making and distributing the liquid product, adopting tolerance factors acceptable by the system. Therefore, once the standard and the tolerances have been set for the products, the devices will establish, in their information base, the verification referring to these characteristics.

Figure 2:
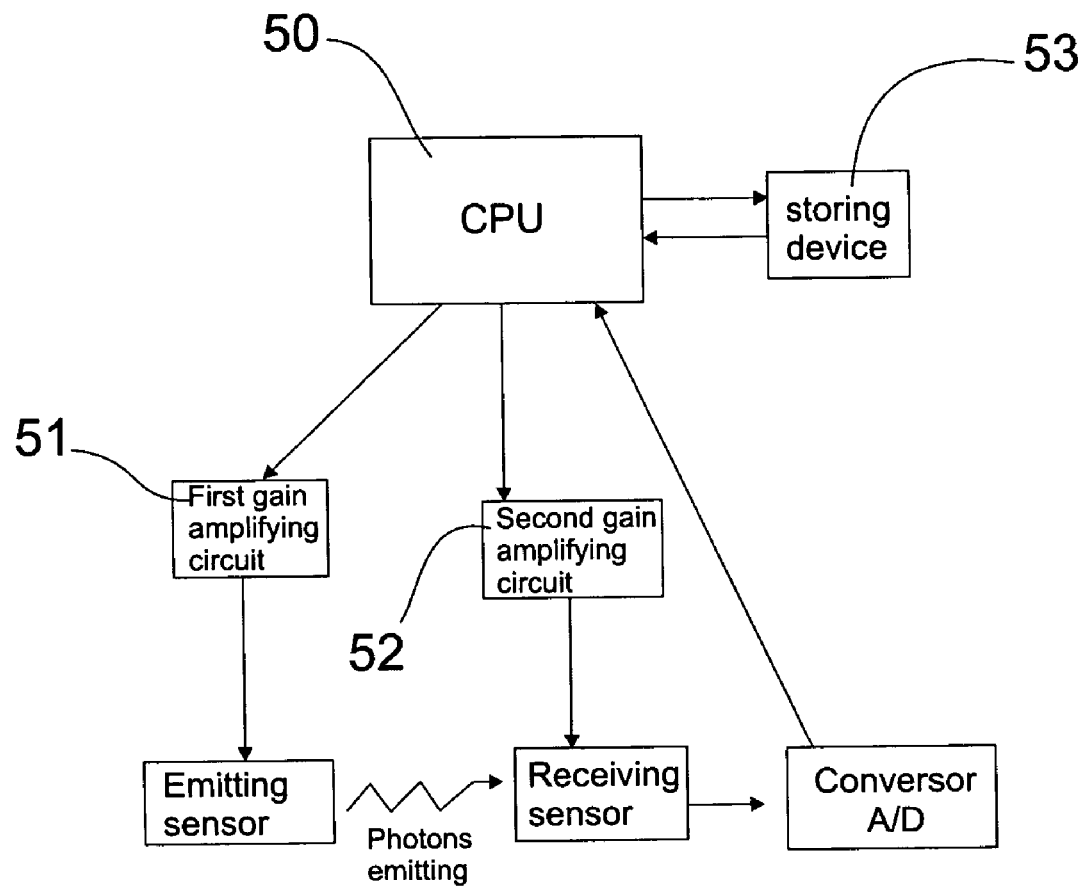
FIG. 2 is a block diagram of the processing and controlling circuit of the device of the present invention.

From the processing and controlling circuit illustrated in FIG. 2, the device carries out, dynamically and automatically, its calibration and the verification of the measurement read, comparing it with the measurement defined as a standard.

Thus, steps 1 and 2 of the calibration described above are carried out by the first and the second gain amplifying circuits 51 and 52, these being totally controlled by the data processing circuit (CPU) 50.

Moreover, the standard values obtained by verifying and reading the standard liquids, and also the levels of tolerance are stored in the data storing device 53 and are used as a basis for comparison with the values obtained by verifying and reading the desired liquids.

In addition to the levels of tolerance of each of the products manufactured, one may also establish the classification of the degree of adulteration as a function of the determination of various levels of variation with respect to the standard set.

Tolerance

The tolerance may be defined by the manufacturer of the combustible liquid, and various criteria may be adopted for establishing tolerances inherent in the process, always taking as a basis the respective variations of the predominant colors.

For instance, if one assigns a tolerance in the Main Color of 10% (system entry), the tolerance in the other will be determined as a function of a factor called Restriction Degree, which may be linked to the value established for the predominant color, that is: High Degree corresponding to a factor of 5 (corresponding to the variation of 5×10%=50%), Middle Degree corresponding to a factor of 3 (corresponding to the variation of 3×10%=30%), Low Degree corresponding to a factor of 2 (corresponding to the variation of 2×10%).

Therefore, the tolerance in the other colors will always be lower (more restrictive) than in the color main component.

Also, the system will verify the degree of variation, thus informing the level of adulteration observed.

Thus, the device may satisfy the various needs of each user, and each one may determine his standard color (registration of his identification).

This means the possibility of verifying the following situations:

A) Dilution of products with colorless substances—the adulteration of products causes a significant attenuation in the non-predominant colors of the product; and B) Mixture of similar products with different color characteristics, which causes a significant variation in the three color components.

This is very common on the present-day market, where fuels having the same functionality (for example, gasoline) are commercialized with different prices depending upon the exhibition of different characteristics (as for example, additive-containing or high-octane gasoline, or else without addition of lead).

The mixture of these products in a fraudulent way on the part of the reseller becomes very attractive, in view of the increase in the margin of profits and with little perception of the difference by the consumer.

These products having different colors (red and green, for example) will result in a mixture with a brown coloring, easily identified by this device of verifying and reading color from a discrepancy with a determined standard value.

For cost economy and utilization of ordinary devices from the market, the curve of response to each of the indicated frequencies may be different, however, this difference will be automatically compensated by the process, in view of the presence of the first gain-amplifying circuit 41, associated to the spectral-frequency emitting sensors 30, 31, 32 and of the second gain-amplifying circuit 42, associated to the spectral-frequency receiving sensors 30', 31', 32'. As already mentioned, these circuits are totally controlled by a data processing circuit (CPU) 40 (FIG. 2).

Thereby one can obtain automatic compensation, so as to carry out the measurement of each of the components of the color.

Another important verification is its capability of distinguishing colors. By using a converter of analog signals into 12-bit digital signals, we have for each component of color a measurement that may vary from 0 to 4095, that is, 5096 graduations of colors.

By adopting this principle, for each of the colors (red, green, blue) we have a possibility of graduation of colors on the order of 4096×4096×4096, that is, 2 raised to the 36th power, that is, 6.87×10 raised to the 10th power graduations referring to the color pallet. In this way, it is possible to obtain a resolution sufficient for a subtle detection of color variations of a liquid product, especially combustible liquids.

As a function of the velocity of response of the system and the processing capacity, it is estimated that one can carry out a reading at every five seconds. This time may be reduced by adopting computing systems having a higher velocity. Thereby one guarantees the measurement and continuous verification of a possible adulteration of the product.

Way of Verifying

A (non-exclusive) way of verifying adulteration of a product is described below:

As described before, each color measurement is associated to a respective light emitter of the corresponding color.

Supposing that the product has a suave orange color, the output of the system may be:
 Value for Red Color: 3792
 Value for Green Color: 1968
 Value for Blue Color: 832

Putting a second product with greenish color, the output of the system may be:
 Value for Red Color: 2720
 Value for Green Color: 3632
 Value for Blue Color: 2320

Upon carrying out numberless tests for the same products, and carrying out the measurement in the same way, the following deviations are achieved:
 For Product 1—Orange Color;
 Deviation of the Red Color: +/−180
 Deviation of the Green Color: +/−40
 Deviation of the Blue Color: +/−23
 For Product 2—Green
 Deviation of Red Color: +/−150
 Deviation of Green Color: +/−85
 Deviation of Blue Color: +/−126

This means that the verifying and reading process will consider the product within the specifications wit the following characteristics:
 For Product 1—Orange Color
 Red Color: Values between 3612 and 3972
 Green Color: Values between 1928 and 2008
 Blue Color: Values between 809 and 855
 For Product 1—Greenish
 Red Color: Values between 2570 and 2870
 Green Color: Values between 3532 and 3717
 Blue Color: Values between 2194 and 2446

Once these standards and associated deviations have been established, the system stores values in its data storing device 53 or non-volatile memory and begins to monitor continuously, through the processing circuit 50, whether the color characteristics of the received products are within the standards set.

For this purpose, the spectral-frequency emitting sensors 30, 31, 32 emit photons at their respective frequencies, which go though the verified liquid and are received with more or less intensity by the corresponding spectral-frequency receiving sensors 30', 31', 32'. The verified values are then compared with the values stored in the data storing device 53 or memory and, if the device detects a variation higher than that determined in one of more components of the color, it immediately informs, warning about a situation of possible adulteration.

Supposing that, in an operation of replenishing the greenish product, the system upon carrying out the monitoring finds the following measurements:
 Red Color: Value equal to 2651 (considered within the Standard)
 Green Color: Value equal to 2034 (out of the Standard)
 Blue Color: Value equal to 1810 (our of the Standard)

Since there was a measurement at least out of set standard, the system considers the product as a whole to out of the specified product.

Predominant Color

Since the readings should have a tolerance and this tolerance may not be considered equal for the three colors, one adopts for each product the definition of the main color component, that it to say, for each product the largest component of the three colors will be considered by the predominant color.

EXAMPLE

Gasoline: Predominant Red Color=Main Component R
Alcohol: Predominant Green Color=Main Component G Behavior of the Colors Once the predominant color has been defined, one may establish that the clarification of the color implies a substantial increase ion the main component and little variation in the two other components. On the contrary, the darkening of the color is based on the substantial decrease of the main component and little variation of the two other non-predominant components.

A preferred embodiment having been described, it should be understood that the scope of the present invention embraces other possible variations, being limited only by the contents of the accompanying claims, which include the possible equivalents.

The invention claimed is:

1. A device of verifying and reading color, particularly used in reading the color of a liquid, the device comprising:
 (a) a guide tube; and
 (b) at least one pair of liquid detection sensors associated to the guide tube,
 the device being characterized by comprising pairs of spectral-frequency emitting sensors and spectral-frequency receiving sensors, associated to the guide tube and oppositely aligned, the spectral-frequency emitting sensors being activated by detection of the liquid by the detection sensors.

2. A device according to claim 1, wherein the guide tube is positioned submerged in the liquid having a coloring.

3. A device according to claim 2, wherein the spectral-frequency emitting sensors are associated to a first surface of the guide tube, and the spectral-frequency receiving sensors are associated to a second surface of the guide tube that is substantially parallel to the first surface.

4. A device according to claim 3, comprises three spectral-frequency emitting sensors that are different from each other, each spectral-frequency emitting sensor emitting photons at frequency ranges different from each other.

5. A device according to claim 4, wherein the frequency range emitted by a spectral-frequency emitting sensor corresponds to a color.

6. A device according to claim 5, comprises three spectral-frequency receiving sensors different from each other, each spectral-frequency receiving sensor receiving the photons emitted by the correspondent spectral-frequency emitting sensors.

7. A device according to claim 6, wherein the intensity in reception of the photon frequency ranges by the spectral-frequency receiving sensors is variable depending upon the coloring of the liquid.

8. A device according to claim 7, wherein the spectral-frequency emitting sensors are associated to a first amplifier electronic circuit.

9. A device according to claim 8, wherein the spectral-frequency receiving sensors are associated to a second amplifier electronic circuit and to a converter of analog signals into digital signals.

10. A device according to claim 9, comprises an information processing and controlling electronic circuit, provided with a data storing device associated to a data processing circuit.

11. A device according to claim 10, wherein the information processing and controlling electronic circuit further comprises a first gain amplifier circuit associated to the spectral-frequency emitting sensors and a second gain amplifier circuit associated to the spectral-frequency receiving sensors, the first and second gain amplifier circuits being controlled by the data processing circuit.

12. A device according to claim 11, wherein the pairs of spectral-frequency emitting sensors and spectral-frequency receiving sensors are positioned at the guide tube equidistantly from each other.

13. A device according to claim 12, wherein the spectral-frequency emitting sensors and the spectral-frequency receiving sensors are positioned in a region substantially close to a lower boundary of the guide tube.

14. A device according to claim 1, wherein the spectral-frequency emitting sensors are provided with red, blue and green colors.

15. A process of verifying the reading color in liquids by means of a device of verifying and reading liquid colors, as defined in claim 1, wherein comprises the following steps:
  (i) calibrating the pairs of spectral-frequency emitting sensors and the spectral-frequency receiving sensors;
  (ii) detecting the liquid by means of the detection sensor;
  (iii) emitting photons at determined frequency ranges of the spectrum by means of the spectral-frequency emitting sensors;
  (iv) receiving the photons by means of the spectral-frequency receiving sensors; and
  (v) reading the frequency received and comparing it with pre-established frequencies.

16. A process according to claim 15, wherein in step (i) it is made an adjustment in the gain of the spectral-frequency emitting sensors and an adjustment in the gain of the spectral-frequency receiving sensors by means of a first gain amplifier circuit and a second gain amplifier circuits.

17. A process according to claim 15, wherein after step (i) and before step (ii), occur a determination of verification and reading parameters on the basis of the standard liquid color and the standard value emission.

18. A process according to claim 17, wherein the standard values are stored in a data storing devices.

19. A process according to claim 15, wherein in step (iv), the photons emitted at the liquid-coloration frequency are filtered and received with a lower intensity, while the photons emitted at the frequencies different from the liquid coloration are received with a higher intensity.

20. A process according to claim 18, wherein in step (v), the values received by the spectral-frequency receiving sensors are compared with the standard values stored in the data storing devices.

* * * * *

UNITED STATES PATENT AND TRADEMARK OFFICE
CERTIFICATE OF CORRECTION

PATENT NO. : 7,130,050 B2
APPLICATION NO. : 10/923104
DATED : October 31, 2006
INVENTOR(S) : Fabricio de Araújo Sacchi It is certified that error appears in the above-identified patent and that said Letters Patent is hereby corrected as shown below:

On the title page:
In ITEM (76) Inventor:
    LINE 3                  change "São Paulo (B" to
                                    --São Paulo (BR)--

In the drawings:
    In FIG. 2,
    lower right-hand text box    change "Conversor A/D" to --Convertor A/D--

Replace FIG. 2 with the following amended figure:

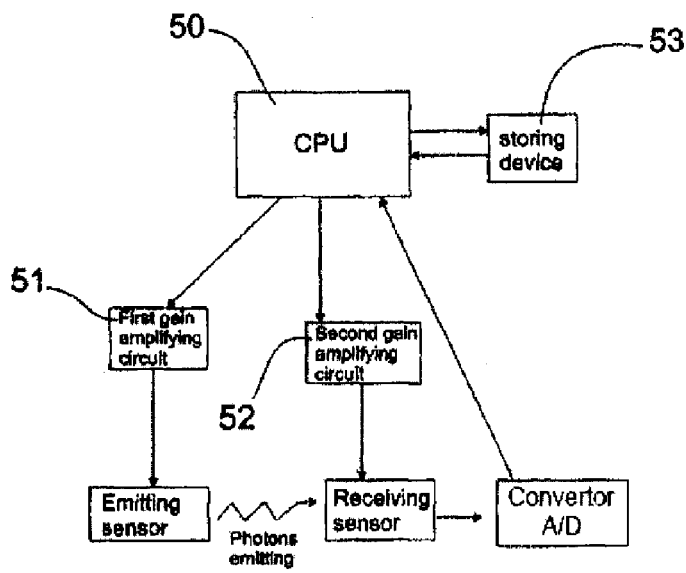

Fig. 2

Signed and Sealed this

Seventh Day of August, 2012

David J. Kappos
*Director of the United States Patent and Trademark Office*

CERTIFICATE OF CORRECTION (continued)
U.S. Pat. No. 7,130,050 B2

| | |
|---|---|
| COLUMN 2, LINE 48, | change "form" to --from-- |
| COLUMN 2, LINE 50, | change "assign to it mark" to --assign it-- |
| COLUMN 6, LINE 62, | change "circuit 41," to --circuit 51,-- |
| COLUMN 6, LINE 64, | change "circuit 42," to-circuit 52,-- |
| COLUMN 6, LINE 67, | change "(CPU) 40" to --(CPU) 50-- |
| COLUMN 8, LINE 8, | change "one of more" to --one or more-- |
| COLUMN 8, LINE 17, | change "(our of the Standard)" to --(out of the Standard)-- |
| COLUMN 8, LINE 25, | change "that it to say," to --that is to say,-- |
| COLUMN 8, LINE 37, | change "ion the main" to --in the main-- |
| CLAIM 4, COLUMN 8, LINE 66, | change "claim 3, comprises" to --claim 3, comprising-- |
| CLAIM 6, COLUMN 9, LINE 6, | change "claim 5, comprises" to --claim 5, comprising-- |
| CLAIM 10, COLUMN 9, LINE 22, | change "claim 9, comprises" to --claim 9, comprising-- |
| CLAIM 18, COLUMN 10, LINE 28, | change "storing devices." to --storing device.-- |
| CLAIM 20, COLUMN 10, LINE 38, | change "storing devices." to --storing device.-- |